US010221344B2

(12) United States Patent
Kasemi et al.

(10) Patent No.: US 10,221,344 B2
(45) Date of Patent: Mar. 5, 2019

(54) AMINE FOR RAPID-CURING EPOXY RESIN COMPOSITIONS

(71) Applicant: SIKA TECHNOLOGY AG, Baar (CH)

(72) Inventors: Edis Kasemi, Zürich (CH); Andreas Kramer, Zürich (CH); Ursula Stadelmann, Zürich (CH); Urs Burckhardt, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

(21) Appl. No.: 15/558,496

(22) PCT Filed: Mar. 23, 2016

(86) PCT No.: PCT/EP2016/056361
§ 371 (c)(1),
(2) Date: Sep. 14, 2017

(87) PCT Pub. No.: WO2016/151006
PCT Pub. Date: Sep. 29, 2016

(65) Prior Publication Data
US 2018/0079710 A1    Mar. 22, 2018

(30) Foreign Application Priority Data
Mar. 23, 2015   (EP) .................................... 15160411

(51) Int. Cl.
| | | |
|---|---|---|
| *C09D 163/00* | (2006.01) | |
| *C08L 63/00* | (2006.01) | |
| *C08G 59/50* | (2006.01) | |
| *C08G 59/64* | (2006.01) | |
| *C07C 213/00* | (2006.01) | |
| *C07C 215/46* | (2006.01) | |
| *C07C 215/48* | (2006.01) | |
| *C07C 215/50* | (2006.01) | |
| *C07C 215/52* | (2006.01) | |
| *C07C 215/54* | (2006.01) | |
| *C09J 163/00* | (2006.01) | |
| *C08G 59/24* | (2006.01) | |
| *C08G 59/36* | (2006.01) | |
| *C08G 59/40* | (2006.01) | |
| *C09D 7/63* | (2018.01) | |
| *B32B 27/38* | (2006.01) | |
| *C08K 5/07* | (2006.01) | |
| *C08K 5/17* | (2006.01) | |

(52) U.S. Cl.
CPC ............. *C09J 163/00* (2013.01); *B32B 27/38* (2013.01); *C07C 215/50* (2013.01); *C08G 59/245* (2013.01); *C08G 59/36* (2013.01); *C08G 59/4007* (2013.01); *C08G 59/5026* (2013.01); *C08G 59/5033* (2013.01); *C08G 59/64* (2013.01); *C08K 5/07* (2013.01); *C08K 5/17* (2013.01); *C08L 63/00* (2013.01); *C09D 7/63* (2018.01); *C09D 163/00* (2013.01); *C07C 2601/14* (2017.05)

(58) Field of Classification Search
None
See application file for complete search history.

(56) References Cited

U.S. PATENT DOCUMENTS

| | | | |
|---|---|---|---|
| 3,068,083 A * | 12/1962 | Gee ........................ | C10L 1/14 252/403 |
| 4,399,268 A | 8/1983 | Becker et al. | |
| 6,465,601 B1 * | 10/2002 | Wiesendanger ... | C08G 18/1816 525/453 |
| 2013/0237681 A1 * | 9/2013 | Burckhardt .......... | C08G 59/504 528/68 |
| 2014/0128506 A1 | 5/2014 | Kramer et al. | |

FOREIGN PATENT DOCUMENTS

| | | |
|---|---|---|
| CN | 103 102 506 A | 5/2013 |
| WO | 2013/010841 A1 | 1/2013 |

OTHER PUBLICATIONS

May 27, 2016 International Search Report issued in International Patent Application No. PCT/EP2016/056361.
Oct. 12, 2018 Office Action issued in European Patent Application No. 16 711 295.2.
International Union of Pure and Applied Chemistry: "IUPAC Gold Bookalkyl groups," 2008, XP055494035, Found on the Internet: URL:https//goldbook.iupac.org/htmi/A/A00228.html [found on Jul. 20, 2018].

* cited by examiner

*Primary Examiner* — Michael J Feely
(74) *Attorney, Agent, or Firm* — Oliff PLC

(57) ABSTRACT

An amine of formula (I) which is particularly suitable for use as a curing agent for epoxy resins. The amine of formula (I) is devoid of non-incorporable toxic phenols, and is low-viscosity and pale in color. It allows the production of easily-workable, low-emission or emission-free epoxy resin products which cure rapidly even at relatively low ambient temperatures thus obtaining a high degree of hardness and a nice surface with hardly any yellowing. This is particularly suited to use in floor or top coatings.

15 Claims, No Drawings

AMINE FOR RAPID-CURING EPOXY RESIN COMPOSITIONS

TECHNICAL FIELD

The invention relates to the field of amines, hardeners for epoxy resins, epoxy resin compositions, and use thereof, especially as coating, covering or coat.

PRIOR ART

In epoxy resin products which are to cure rapidly even at relatively low ambient temperatures, in the range from 0 to 10° C., for instance, it is common for what are called Mannich bases to be used as hardeners. Mannich bases constitute condensation products of phenols, aldehydes, and polyamines, which are capable of rapid reaction with epoxy resins, causing epoxy resin products to rapidly develop strength and become tack-free even at low ambient temperatures, and therefore to be robust even shortly after application.

Mannich bases according to the prior art typically include a considerable fraction (up to around 50 weight %) of phenols, more particularly phenol or alkylphenols such as cresol, tert-butylphenol or nonylphenol. Phenols of this kind are toxic substances which are not incorporated into the epoxy resin in the course of the curing reaction. Owing to a greater emphasis being placed on EHS aspects by professional bodies and consumers, and also in view of more stringent state regulation, phenol-containing hardeners have come under pressure. Ways have therefore been sought for preparing phenol-free Mannich bases. The removal of the phenols from conventional Mannich bases via physical operations, however, is costly and inconvenient, and of virtually no commercial interest. Reducing the phenol content via the chemical operating regime, in particular through a lower phenol/polyamine ratio, typically results in dark-colored Mannich bases which are of high viscosity and include high fractions of polyamine-bridged polycyclic compounds. Hardeners of this kind can be used only in applications where hue is not critical, such as in primers, for example, and have to be diluted in order to be worked, either by means of (VOC) solvents or thinners, thus giving rise to further EHS problems, or using low-viscosity polyamines, something which results usually in blushing effects. "Blushing effects" are surface defects which appear in the course of curing, such as cloudiness, spots, roughness, and stickiness, which are caused by salt formation ("blushing") of amines with carbon dioxide ($CO_2$) from the air and which appear particularly under high atmospheric humidity and at low temperatures.

U.S. Pat. No. 4,399,268 describes hardeners containing phenol groups for epoxy resins with high chemical stability. The hardeners disclosed are prepared by reductive alkylation of polyamines with aldehydes containing phenol groups, and are phenol-free. However, they are of decidedly high viscosity and result in more severe yellowing.

WO 2013/010841 likewise describes hardeners containing phenol groups for epoxy resins, arising from reductive alkylation. The hardeners disclosed are phenol-free and have a low viscosity, but are not without room for improvement in terms of cure rate and viscosity.

PRESENTATION OF THE INVENTION

It is an object of the present invention, therefore, to provide a hardener with high reactivity for epoxy resins that is phenol-free and of low viscosity, that reacts rapidly with epoxy resins, even at low ambient temperatures, that does not lead to blushing effects, that is light in color and that does not cause more severe yellowing.

This object, surprisingly, is achieved with the amine of the formula (I) as described in claim 1. The amine of the formula (I) can be prepared in phenol-free form in a simple process from readily available starting materials and is of surprisingly low viscosity. It reacts with epoxy resins at a high rate, both at room temperature and at lower temperatures, without blushing effects occurring, and therefore enables rapid development of strength and high product quality even under adverse conditions of use. Particularly surprising is the fact that the amine of the formula (I) can be prepared in virtually colorless form and leads to extraordinarily low yellowing of epoxy resin products after curing. The amine dilutes epoxy resins surprisingly well, better than similar amines from the prior art. As a hardener for epoxy resins, it allows very rapid development of strength, even at relatively low temperatures such as at 8° C., for example, to give high-quality plastics of high hardness and an even, non-tacky surface with high gloss. By virtue of its pale color, consequences of preparation in accordance with the invention and of low yellowing, it can be used without limitation even in products which are demanding in terms of color, such as topcoats or floor coverings. In comparison with similar amines known from the prior art, the amine of the formula (I) enables epoxy resin compositions having a particularly attractive combination of low viscosity and rapid development of strength, a combination which could not have been expected from the prior art.

By virtue of its low viscosity, the amine of the formula (I) can also be used without the employment of diluents, and therefore permits the formulation of low-emission epoxy resin products, more particularly epoxy resin coatings.

Further aspects of the invention are subjects of further independent claims. Particularly preferred embodiments of the invention are subjects of the dependent claims.

CERTAIN EMBODIMENTS OF THE INVENTION

A subject of the invention is an amine of the formula (I),

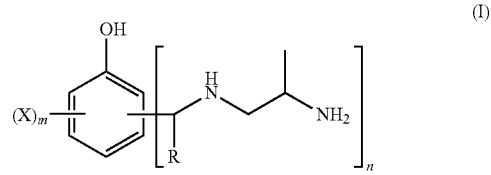

where
m is 0 or 1 or 2,
n is 1 or 2 or 3,
R is a hydrogen radical or alkyl radical having 1 to 8 carbon atoms or phenyl radical, and
X represents identical or different radicals selected from the group consisting of hydroxyl and alkyl, alkenyl and alkoxy having in each case 1 to 18 carbon atoms, and optionally containing ether oxygen, hydroxyl oxygen or amine nitrogen.

Substance names beginning with "poly", such as polyamine, polyol or polyepoxide, denote substances which formally contain per molecule two or more of the functional groups that occur in their name.

A "primary amino group" is an NH$_2$ group which is bonded to an organic radical, and a "secondary amino group" is an NH group which is bonded to two organic radicals, which may also together be part of a ring.

The "amine hydrogen" refers to the hydrogen atoms of primary and secondary amino groups.

"Amine hydrogen equivalent weight" is the weight fraction of a hardener or of an amine per amine hydrogen present in the hardener or amine.

A "diluent" is a substance which is soluble in an epoxy resin and lowers its viscosity and which is not incorporated covalently into the resin matrix when the epoxy resin is cured.

The term "viscosity" refers to the dynamic viscosity or shear viscosity, which is defined by the ratio between the shearing stress and the shear rate (rate gradient) and is determined as described in the working examples.

"Molecular weight" refers to the molar mass (in grams per mole) of a molecule. "Average molecular weight" is the numerical average $M_n$ of an oligomeric or polymeric mixture of molecules, and is determined customarily by means of gel permeation chromatography (GPC) against polystyrene as standard.

"Room temperature" refers to a temperature of 23° C.

A substance or composition referred to as "phenol-free" is one which is free from phenol or alkylphenols such as kresol, tert-butylphenol or nonylphenol, for example, or contains at most traces of such phenols in a concentration below 0.1 weight %.

Preferably X represents identical or different radicals selected from the group consisting of hydroxyl and alkyl, alkenyl, and alkoxy having in each case 1 to 15 carbon atoms and optionally containing ether oxygen, hydroxyl oxygen or amine nitrogen.

With particular preference X is hydroxyl, methyl, methoxy, tert-butyl, nonyl, dodecyl, pentadeca-8,11,14-trienyl, N,N-dimethylaminomethyl, N,N-diethylamino-methyl, N-methyl-N-ethylaminomethyl, N-methyl-N-butyl-aminomethyl, N,N-bis(hydroxyethyl)aminomethyl, N-methyl-N-hydroxyethylaminomethyl, N-ethyl-N-hydroxyethylaminomethyl, N-butyl-N-hydroxyethylaminomethyl, N-pyrrolidinylmethyl, N-piperidinylmethyl, N-morpholinylmethyl, (3-(N,N-dimethylamino)propyl)aminomethyl or (3-(3-(N,N-dimethylamino)propyl)aminopropyl)aminomethyl, more particularly hydroxyl, methoxy, or N,N-dimethylaminomethyl.

R preferably is a hydrogen radical or is an alkyl radical having 1 to 4 carbon atoms, more particularly methyl, ethyl, isopropyl or 3-heptyl, or is a phenyl radical.

With particular preference R is a hydrogen radical or is a methyl radical, and more particularly is a hydrogen radical.

The preferred amines of the formula (I) are notable for particular ease of preparability, particularly low viscosity, and particularly good properties for the uses described.

With particular preference m is 0 or 1, n is 1, and R is a hydrogen radical or methyl radical. X in this case is more particularly hydroxyl or methoxy. An amine of the formula (I) of this kind can be prepared in particularly pure form, is of particularly low viscosity, and is particularly reactive.

With further particular preference, (m+n) is 3, R is a hydrogen radical, and X is an N,N-dialkyl radical which optionally contains one or two hydroxyl groups, or is an N-alkyl radical which optionally contains a hydroxyl group or one or two amine nitrogens, or is an N-pyrrolidinylmethyl or N-piperidinylmethyl or N-morpholinylmethyl radical.

More particularly (m+n) is 3, R is a hydrogen radical, and X is N,N-dimethylaminomethyl.

An amine of the formula (I) of this kind is particularly easy to prepare and of particularly low viscosity.

Very preferably the amine of the formula (I) is selected from the group consisting of 2-(((2-aminopropyl)amino)methyl)phenol, 2-(1-((2-aminopropyl)-amino)ethyl)phenol, 2-(((2-aminopropyl)amino)methyl)-4,6-bis(dimethylaminomethyl)phenol, 4-(((2-amino-propyl)amino)methyl)-2,6-bis(dimethylminomethyl)phenol, 2,4-bis(((2-aminopropyl)amino)methyl)-6-dimethylaminomethylphenol, 2,6-bis(((2-aminopropyl)amino)methyl)-4-dimethylaminomethylphenol and 2,4,6-tris(((2-aminopropyl)amino)methyl)phenol.

In this context, 2-(((2-aminopropyl)amino)methyl)phenol and 2-(1-((2-aminopropyl)amino)ethyl)phenol are notable for particularly high reactivity, a particularly low viscosity, and particularly low propensity toward blushing effects, this being particularly advantageous for use in epoxy resin coatings.

2-(((2-Aminopropyl)amino)methyl)-4,6-bis(dimethylamino-methyl)phenol, 4-(((2-aminopropyl)amino)methyl)-2,6-bis(dimethylaminomethyl)phenol, 2,4-bis(((2-aminopropyl)amino)methyl)-6-dimethylaminomethylphenol and 2,6-bis(((2-aminopropyl)amino)methyl)-4-dimethylaminomethylphenol are notable for particular ease of preparation and particularly high reactivity with epoxy resins.

2,4,6-Tris(((2-aminopropyl)amino)methyl)phenol is notable for particular ease of preparation and particularly high functionality in respect of amine hydrogens.

A further subject of the invention is a process for preparing the amine of the formula (I), in which 1,2-propylenediamine is reacted
either, with reductive alkylation, with at least one aldehyde or ketone of the formula (II) and hydrogen

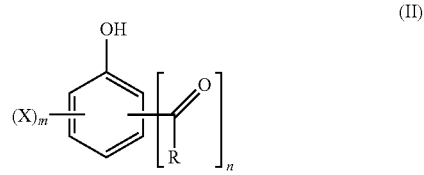

or, with transamination, with a Mannich base of the formula (III)

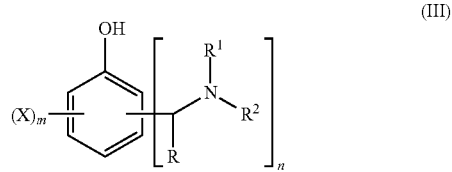

where
$R^1$ and $R^2$ are each identical or different alkyl, cycloalkyl or aralkyl radicals having 1 to 4 carbon atoms and optionally containing ether oxygen or amine nitrogen, or together are an alkylene radical having 4 to 8 carbon atoms and optionally containing ether oxygen or amine nitrogen,
and m, n, X, and R have the definitions already stated.

Reaction products obtained from this process are phenol-free, have a high content of amines of the formula (I), and are particularly suitable for use as hardeners for epoxy resins.

The reaction product comprising at least one amine of the formula (I) from the process described can be used without further workup or purification as a hardener for epoxy resins, or a purification step may be carried out before it is used further.

In formula (II) n is preferably 1.

In formula (III) (m+n) is preferably 3.

$R^1$ and $R^2$ preferably, independently of one another, are each methyl, ethyl, isopropyl, butyl or isobutyl, or together are 1,4-butylene or 1,5-pentylene or 3-oxa-1,5-pentylene.

With particular preference $R^1$ and $R^2$ are each methyl.

The process variant of the reductive alkylation of 1,2-propylenediamine with the aldehyde or ketone of the formula (II) may take place directly with molecular hydrogen or indirectly by transfer of hydrogen from other reagents. Preference is given to using molecular hydrogen. The reaction conditions are advantageously selected such that only one of the two amino groups of 1,2-propylenediamine is singly alkylated with high selectivity, and the aromatic ring is not hydrogenated. Operation takes place preferably under a hydrogen pressure of 5 to 100 bar, at a temperature of 40 to 120° C., and in the presence of a suitable catalyst. Preferred as catalyst are palladium on carbon (Pd/C), platinum on carbon (Pt/C), Adams catalyst or Raney nickel, more particularly palladium on carbon or Raney nickel. The preparation of the amine of the formula (I) by reductive alkylation is particularly advantageous for use as hardener for epoxy resins, since primary amines are singly alkylated with high selectivity, while secondary amino groups are barely alkylated further. The reaction product may therefore be used without further workup or purification as a hardener for epoxy resins.

In one embodiment of the reductive alkylation, 1,2-propylenediamine is used in a molar ratio of about 1/1 relative to the aldehyde or ketone of the formula (II). In this case 1,2-propylenediamine is preferably dissolved in a solvent, which is removed by distillation after the reaction. This preparation is particularly economic. An amine of the formula (I) prepared in this way has certain fractions of further alkylation products, as shown by way of example in the formulae below for the case where the index n is 1:

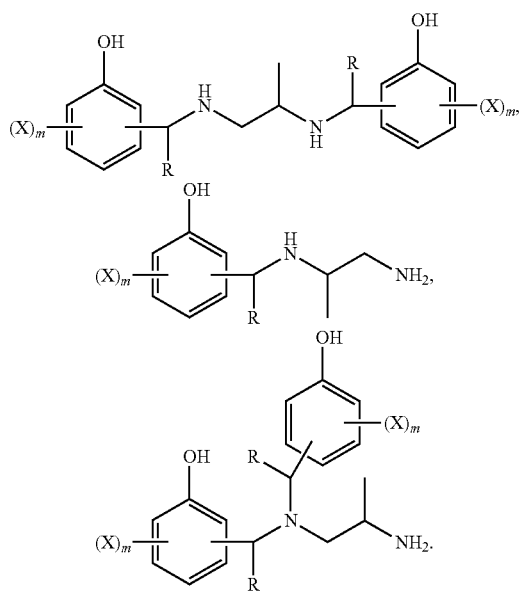

Preferably, 1,2-propylenediamine is used in a stoichiometric excess over the aldehyde or ketone of the formula (II), and the excess is removed, in particular by distillation, before or—preferably—after the reduction.

The reductive alkylation is carried out preferably with a ratio between the number of 1,2-propylenediamine molecules and the number of aldehyde or ketone groups in the aldehyde or ketone of the formula (II) of at least 1.5/1, more preferably at least 2/1. Following removal of 1,2-propylenediamine, a reaction product of this kind includes a particularly high fraction of amine of the formula (I).

Suitability as aldehyde or ketone of the formula (II) is possessed in particular by 2-hydroxybenzaldehyde (salicylaldehyde), 3-hydroxybenzaldehyde, 4-hydroxybenzaldehyde, 2-hydroxy-3-methylbenzaldehyde, 2-hydroxy-5-methylbenzaldehyde, 4-hydroxy-3,5-dimethylbenzaldehyde, 2-hydroxy-3-methoxybenzaldehyde (o-vanillin), 2-hydroxy-4-methoxybenzaldehyde, 2-hydroxy-5-methoxybenzaldehyde, 3-hydroxy-4-methoxybenzaldehyde (isovanillin), 4-hydroxy-2-methoxybenzaldehyde, 4-hydroxy-3-methoxybenzaldehyde (vanillin), 6-hydroxy-2,4-dimethoxybenzaldehyde 2,3-dihydroxybenzaldehyde, 2,4-dihydroxybenzaldehyde (β-resorcinaldehyde), 2,5-dihydroxybenzaldehyde (gentisinaldehyde), 3,4-dihydroxybenzaldehyde, 3,5-dihydroxybenzaldehyde, 2,3,4-trihydroxybenzaldehyde, 2'-hydroxyacetophenone, 3'-hydroxyacetophenone, 4'-hydroxyacetophenone, 4'-hydroxy-3'-methoxyacetophenone (acetovanillone), 4'-hydroxy-3',5'-dimethoxyacetophenone, 2',4'-dihydroxyacetophenone (resacetophenone), 2',5'-dihydroxyacetophenone (quinacetophenone), 2',6'-dihydroxyacetophenone (2-acetylresorcinol), 2',4'-dihydroxyacetophenone, 4-hydroxybenzophenone or 2-hydroxy-4-methoxybenzophenone.

Preferred as aldehyde or ketone of the formula (II) are salicylaldehyde, 3-hydroxybenzaldehyde, 4-hydroxybenzaldehyde, o-vanillin, isovanillin, vanillin, (β-resorcinaldehyde, gentisinaldehyde, 3,4-dihydroxybenzaldehyde, 2'-hydroxyacetophenone, 3'-hydroxyacetophenone, 4'-hydroxyacetophenone, acetovanillone or resacetophenone, more particularly salicylaldehyde or 2'-hydroxyacetophenone.

The reductive alkylation carried out with salicylaldehyde or 2'-hydroxyacetophenone as aldehyde or ketone of the formula (II) is preferred.

An amine of the formula (I) from this process has a high purity and is notable for particularly low viscosity, low intrinsic coloration, and high reactivity. In this case, preferably, m is 0 or 1, n is 1 and R is a hydrogen or methyl radical.

The process variant of the transamination of a Mannich base of the formula (III) with 1,2-propylenediamine releases an amine $R^1$—NH—$R^2$. This amine is preferably removed from the reaction mixture, in particular by means of distillation.

The amine $R^1$—NH—$R^2$ released preferably has a lower boiling point than 1,2-propylenediamine. In that case, the reaction mixture is preferably heated at reflux and at atmospheric pressure during the reaction, with the cooling water being at a temperature at which 1,2-propylenediamine is condensed, but not the amine $R^1$—NH—$R^2$ released. Operation takes place preferably at a temperature of 60 to 140° C.

The reaction conditions of the transamination are advantageously selected such that only one of the two amino groups of 1,2-propylenediamine is alkylated and hence as little as possible of polycyclic compounds is formed.

The transamination is carried out preferably with a ratio between the number of 1,2-propylenediamine molecules and the number of aminoalkyl substituents in the Mannich base of the formula (III) of at least 1/1, more particularly at least 1.5/1, more preferably at least 2/1.

In one preferred embodiment of the transamination, 1,2-propylenediamine is used stoichiometrically relative to the number of aminoalkyl substituents in the Mannich base, and the amine R$^1$—NH—R$^2$ released is removed during or after the reaction from the reaction mixture, more particularly by means of distillation. This preparation is particularly economic.

In one particularly preferred embodiment of the transamination, 1,2-propylenediamine is used in a stoichiometric excess over the number of aminoalkyl substituents in the Mannich base, and the excess is removed after the reduction, in particular by means of distillation. In this case the ratio between the number of 1,2-propylenediamine molecules and the number of aminoalkyl substituents in the Mannich base is preferably at least 1.5/1, more preferably at least 2/1. The reaction product thus obtained has a particularly high fraction of amine of the formula (I) and a particularly low fraction of polycyclic byproducts.

Especially suitable as Mannich base of the formula (III) are reaction products of at least one phenol with at least one aldehyde and at least one secondary amine by known processes.

Suitability as phenol is possessed in particular by phenol, o-cresol, m-cresol, p-cresol, 4-tert-butylphenol, 4-nonylphenol, 4-dodecylphenol, 3-(pentadeca-8,11,14-trienyl)phenol (cardanol), 2,3-dimethylphenol (o-xylenol), 2,4-dimethylphenol (m-xylenol), 2,5-dimethylphenol (p-xylenol), 2,6-dimethylphenol, 3,4-dimethylphenol, 3,5-dimethylphenol, 2-methoxyphenol (guaiacol), 3-methoxyphenol, 4-methoxyphenol, 2,6-dimethoxyphenol, pyrocatechol, resorcinol, hydroquinone or pyrogallol. Preference is given to phenol, o-cresol, m-cresol, p-cresol, 4-tert-butylphenol, 4-nonylphenol, 4-dodecylphenol, cardanol, o-xylenol, m-xylenol, p-xylenol, guaiacol, 3-methoxyphenol, 4-methoxyphenol, resorcinol or hydroquinone. Particular preference is given to phenol, o-cresol, m-cresol, p-cresol, cardanol or resorcinol, more particularly phenol or cardanol.

Particular suitability as aldehyde is possessed by formaldehyde, acetaldehyde, propionaldehyde, iso-butyraldehyde, 2-ethylhexanal or benzaldehyde. Formaldehyde is preferred.

Particular suitability as secondary amine is possessed by dimethylamine, diethylamine, diisopropylamine, dibutylamine, diisobutylamine, methylethylamine, methylbutylamine, pyrrolidine, piperidine, morpholine. Dimethylamine is preferred.

A particularly preferred Mannich base of the formula (III) is 2,4,6-tris(N,N-dimethylaminomethyl)phenol.

This Mannich base can be prepared particularly well and from advantageous raw materials, is available commercially in high quality (high purity, phenol-free), and is particularly suitable for transamination reactions, since the dimethylamine it releases has a low boiling point and can therefore be removed selectively from the reaction mixture in the presence of 1,2-propylenediamine.

The transamination preferably is carried out with 2,4,6-tris(N,N-dimethylaminomethyl)phenol as Mannich base of the formula (III).

An amine of the formula (I) from this process is notable for high purity, high functionality in respect of amine hydrogens, low viscosity, and low intrinsic coloration.

Preferably in this case (m+n) is 3, R is a hydrogen radical, and X in particular is N—N-dimethylamino-methyl.

The process involving transamination with 2,4,6-tris(N, N-dimethylaminomethyl)phenol can be carried out such that not all three aminoalkyl substituents are replaced, thus giving, in particular, products as shown by way of example in the formulae below:

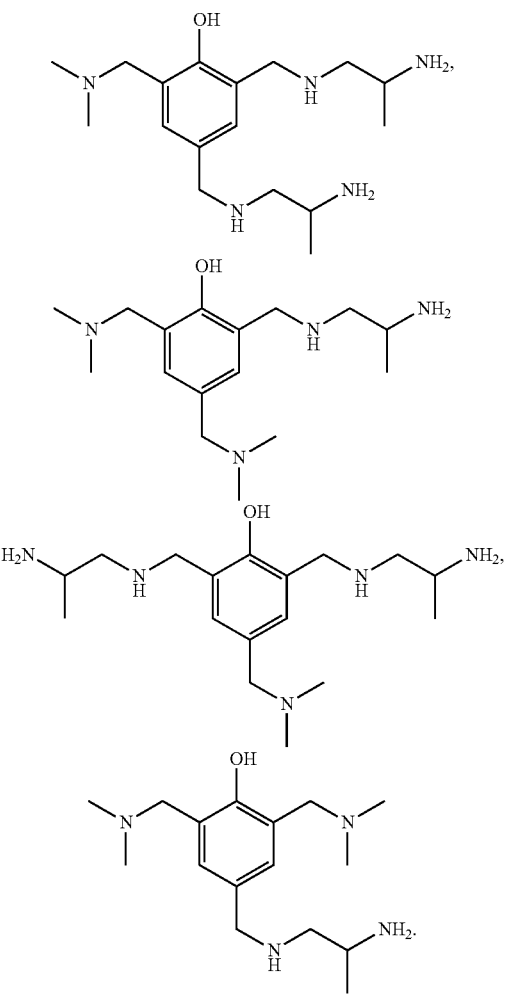

These products represent amines of the formula (I) in which X is dimethylaminomethyl and (m+n) is 3.

A reaction product from the transamination with 2,4,6-tris(N,N-dimethylaminomethyl)phenol typically comprises a mixture of such amines of the formula (I) and the fully transaminated product 2,4,6-tris(((2-aminopropyl)amino)methyl)phenol, where the fraction of only partially transaminated products can be controlled by means of the stoichiometry, the reaction time and/or the way in which the dimethylamine released is removed. Likewise included, typically, are fractions of polycyclic compounds.

The amine of formula (I) is particularly suitable as a hardener for epoxy resins. It has a viscosity which is low for amines containing phenol groups, and allows readily workable epoxy resin products of low viscosity which cure rapidly even at relatively low ambient temperatures to form a high level of hardness and an attractive—i.e., even and non-tacky—surface, with virtually no yellowing.

A further subject of the invention is therefore the use of at least one amine of the formula (I) as hardener for epoxy resins.

A preferred hardener for epoxy resins comprises, in addition to the amine of the formula (I), further constituents, more particularly further amines and/or additives. A further subject of the invention is therefore a hardener for epoxy resins, comprising at least one amine of the formula (I) and at least one further amine and/or at least one additive. The further amine in this case is not an amine of the formula (I).

Especially suitable as further amine are polyamines which have at least two, more particularly at least three, amine hydrogens reactive toward epoxide groups, more particularly the following polyamines:

aliphatic, cycloaliphatic or arylaliphatic primary diamines, especially 2,2-dimethyl-1,3-propanediamine, 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2(4),4-trimethylhexamethylenediamine (TMD), 1,7-heptanediamine, 1,8-octanediamine, 1,9-nonanediamine, 1,10-decanediamine, 1,11-undecanediamine, 1,12-dodecanediamine, 1,2-, 1,3- or 1,4-diaminocyclohexane, bis(4-aminocyclohexyl)methane ($H_{12}$-MDA), bis(4-amino-3-methylcyclohexyl)methane, bis(4-amino-3-ethylcyclohexyl)methane, bis(4-amino-3,5-dimethyl-cyclohexyl)methane, bis(4-amino-3-ethyl-5-methyl-cyclohexyl)methane, 1-amino-3-aminomethyl-3,5,5-trimethylcyclohexane (isophoronediamine or IPDA), 2- or 4-methyl-1,3-diaminocyclohexane or mixtures thereof, 1,3-bis(aminomethyl)cyclohexane, 1,4-bis (aminomethyl)cyclohexane, 2,5(2,6)-bis(aminomethyl)-bicyclo[2.2.1]heptane (NBDA), 3(4),8(9)-bis(amino-methyl)tricyclo[5.2.1.0$^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]-undecane, 1,3-bis(aminomethyl)benzene (MXDA) or 1,4-bis(aminomethyl)benzene;

aliphatic, cycloaliphatic or arylaliphatic primary triamines, especially 4-aminomethyl-1,8-octanediamine, 1,3,5-tris(aminomethyl)benzene, 1,3,5-tris (aminomethyl)cyclohexane, tris(2-aminoethyl)amine, tris(2-aminopropyl)amine or tris(3-aminopropyl)amine;

aliphatic primary di- or triamines containing ether groups, especially bis(2-aminoethyl) ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxatridecane-1,13-diamine or higher oligomers of these diamines, bis(3-aminopropyl) polytetrahydrofurans or other polytetra-hydrofurandiamines, cycloaliphatic ether group-containing diamines from the propoxylation and subsequent amination of 1,4-dimethylolcyclohexane, obtainable in particular as Jeffamine® RFD-270 (from Huntsman), or polyoxyalkylenedi- or -triamines, which typically represent products from the amination of polyoxyalkylenedi- or -triols and are obtainable, for example, under the name Jeffamine® (from Huntsman), under the name Polyetheramine (from BASF) or under the name PC Amine® (from Nitroil). Especially suitable polyoxyalkylenedi- or -triamines are Jeffamine® D-230, Jeffamine® D-400, Jeffamine® D-2000, Jeffamine® EDR-104, Jeffamine® EDR-148, Jeffamine® EDR-176, Jeffamine® T-403, Jeffamine® T-3000, Jeffamine® T-5000, or corresponding amines from BASF or Nitroil;

polyamines containing secondary amino groups and having two primary aliphatic amino groups, such as, in particular, 3-(2-aminoethyl)aminopropylamine, bis(hexamethylene)triamine (BHMT), diethylenetriamine (DETA), triethylenetetramine (TETA), tetraethylenepentamine (TEPA), pentaethylenehexamine (PEHA) or higher homologs of linear polyethyleneamines such as polyethylenepolyamine having 5 to 7 ethyleneamine units (referred to as "higher ethylenepolyamine", HEPA), products from the multiple cyanoethylation or cyanobutylation and subsequent hydrogenation of primary di- and polyamines having at least two primary amino groups, such as dipropylenetriamine (DPTA), N-(2-aminoethyl)-1,3-propanediamine (N3-amine), N,N'-bis(3-aminopropyl)ethylenediamine (N4-amine), N,N'-bis(3-aminopropyl)-1,4-diaminobutane, N5-(3-aminopropyl)-2-methyl-1,5-pentanediamine, N3-(3-aminopentyl)-1,3-pentanediamine, N5-(3-amino-1-ethylpropyl)-2-methyl-1,5-pentanediamine or N,N'-bis(3-amino-1-ethylpropyl)-2-methyl-1,5-pentanediamine;

polyamines having one or two secondary amino groups, especially products from the reductive alkylation of primary aliphatic polyamines with aldehydes or ketones, especially $N^1$-benzyl-1,2-propanediamine, $N^1$-(4-methoxybenzyl)-1,2-propanediamine, N-benzyl-1,3-bis(aminomethyl)benzene, N,N'-dibenzyl-1,3-bis(amino-methyl)benzene, N-2-ethylhexyl-1,3-bis(aminomethyl)-benzene, N,N'-bis(2-ethylhexyl)-1,3-bis(aminomethyl)-benzene, or partially styrenized polyamines such as, in particular, partially styrenized MXDA (available as Gaskamine® 240 from Mitsubishi Gas Chemical);

aromatic polyamines, such as, in particular, m- and p-phenylenediamine, 4,4'-, 2,4' and/or 2,2'-diaminodiphenylmethane, 3,3'-dichloro-4,4'-diaminodiphenylmethane (MOCA), 2,4- and/or 2,6-tolylenediamine, mixtures of 3,5-dimethylthio-2,4- and -2,6-tolylenediamine (available as Ethacure® 300 from Albermarle), mixtures of 3,5-diethyl-2,4- and -2,6-tolylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenyl sulfone (DDS), 4-amino-N-(4-aminophenyl)benzene-sulfonamide, 5,5'-methylenedianthranilic acid, dimethyl 5,5'-methylenedianthranilate, 1,3-propylene bis(4-aminobenzoate), 1,4-butylene bis(4-aminobenzoate), polytetramethylene oxide bis(4-aminobenzoate) (available as Versalink® from Air Products), 1,2-bis(2-aminophenylthio)ethane, 2-methylpropyl 4-chloro-3,5-diaminobenzoate or tert-butyl 4-chloro-3,5-diaminobenzoate;

adducts of the stated polyamines with epoxides or epoxy resins, especially adducts with diepoxides having a molar ratio of approximately 2/1, adducts with monoepoxides having a molar ratio of approximately 1/1, or reaction products of amines and epichlorohydrin, more particularly that of 1,3-bis(aminomethyl)benzene, available commercially as Gaskamine® 328 (from Mitsubishi Gas Chemical);

polyamidoamines, especially reaction products of a mono- or polybasic carboxylic acid, and/or the esters or anhydrides thereof, particularly of a dimer fatty acid, with an aliphatic, cycloaliphatic or aromatic polyamine that is used in a stoichiometric excess, more particularly a polyalkyleneamine such as, for example, DETA or TETA, more particularly the commercially available polyamidoamines Versamid® 100, 125, 140 or 150 (from Cognis), Aradur® 223, 250 or 848 (from Huntsman), Euretek® 3607 or 530 (from Huntsman) or Beckopox® EH 651, EH 654, EH 655, EH 661 or EH 663 (from Cytec); or phenalkamines, i.e., Mannich bases of cardanol (long-chain alk(en)yl-phenols and -resourcinols obtained by thermal treatment of cashew shell oil extracts, comprising as principal component 3-(pentadeca-8,11,14-trienyl)phenol), especially the commercially available phenalkamines Cardolite® NC-541, NC-557, NC-558, NC-566, Lite 2001, Lite 2002, NX-5607 or NX-5608 (from Cardolite), Aradur® 3440, 3441, 3442 or 3460 (from Huntsman) or Beckopox® EH 614, EH 621, EH 624, EH 628 or EH 629 (from Cytec).

Preferably the further amine is selected from the group consisting of 2-butyl-2-ethyl-1,5-pentanediamine (C11 neodiamine), 2,2(4),4-trimethylhexamethylenediamine (TMD), 1,12-dodecandiamine, bis(4-aminocyclohexyl)-methane ($H_{12}$-MDA), 1-amino-3-aminomethyl-3,5,5-trimethylcyclohexane (isophoronediamine or IPDA), 1,3-bis(aminomethyl)cyclohexane, 1,4-bis(aminomethyl)-cyclohexane, 2,5 (2,6)-bis(aminomethyl)bicyclo[2.2.1]-heptane (NBDA), 3(4),8(9)-bis(aminomethyl)tricyclo[5.2.1.0$^{2,6}$]decane, 1,4-diamino-2,2,6-trimethylcyclohexane (TMCDA), 1,8-menthanediamine, 3,9-bis(3-aminopropyl)-2,4,8,10-tetraoxaspiro[5.5]undecane, 1,3-bis(aminomethyl)benzene (MXDA), aliphatic primary di- and triamines containing ether groups, N-benzyl-1,2-propanediamine, $N^1$-(4-methoxybenzyl)-1,2-propanediamine, N-benzyl-1,3-bis(aminomethyl)benzene, N,N'-dibenzyl-1,3-bis(aminomethyl)benzene, N-2-ethylhexyl-1,3-bis(aminomethyl)benzene, N,N'-bis(2-ethylhexyl)-1,3-bis(aminomethyl)benzene, partially styrenized 1,3-bis(aminomethyl)benzene, and adducts of (i) at least one polyamine having at least three amine hydrogens that are reactive toward epoxide groups with (ii) at least one epoxide.

Preference is given to TMD, IPDA, NBDA or MXDA. These further amines are of low volatility and, together with the amine of the formula (I), enable readily processable, rapidly curing epoxy resin products of high hardness and stability with attractive surfaces.

Preferred, moreover, are ether-group-containing aliphatic primary di- and triamines, more particularly polyoxyalkylene di- or -triamines having an average molecular weight in the range from 200 to 500 g/mol, especially Jeffamine® D-230 or Jeffamine® T-403 (both from Huntsman), or cycloaliphatic ether-group-containing diamines from the propoxylation and subsequent amination of 1,4-dimethylolcyclohexane, especially Jeffamine® RFD-270 (from Huntsman). These further amines, together with the amine of the formula (I), enable readily processable epoxy resin products of low brittleness with reliable curing to high ultimate hardness without so-called "freezing". "Freezing" refers to the phenomenon whereby, after initially good development of hardness, an epoxy resin composition fails to cure to the anticipated ultimate hardness at a given temperature, the curing instead remaining at a relatively low hardness. Such effects occur in particular at low curing temperatures.

Preference is given further to $N^1$-benzyl-1,2-propanediamine, N-(4-methoxybenzyl)-1,2-propanediamine, N-benzyl-1,3-bis(aminomethyl)benzene, N,N'-dibenzyl-1,3-bis (aminomethyl)benzene, N-2-ethylhexyl-1,3-bis (aminomethyl)benzene, N,N'-bis(2-ethylhexyl)-1,3-bis (aminomethyl)benzene or partially styrenized 1,3-bis (aminomethyl)benzene, especially the commercially available Gaskamine® 240 (from Mitsubishi Gas Chemical). These further amines, together with the amine of the formula (I), enable epoxy resin products of particularly low viscosity and therefore good processability, with particularly attractive surfaces.

Additionally preferred are adducts of (i) at least one polyamine, having at least three amine hydrogens reactive toward epoxide groups, with (ii) at least one epoxide.

Preferred as polyamine for such an adduct are the aforementioned polyamines having at least three amine hydrogens that are reactive toward epoxide groups, or smaller polyamines such as, in particular, ethylenediamine, the isomeric propylenediamines or the isomeric butylenediamines.

Preferred as epoxide for such an adduct are diepoxides, such as, in particular, bisphenol A or F or A/F diglycidyl ether, poly-1,2-propylene oxide diglycidyl ether or monoepoxides. Particularly preferred are aromatic monoepoxides, especially cresyl glycidyl ether, tert-butylphenyl glycidyl ether or the glycidyl ether of cardanol. Particularly preferred is cresyl glycidyl ether. Suitable cresyl glycidyl ethers are all isomeric cresyl glycidyl ethers or mixtures thereof, more particularly commercially available types such as, in particular, Araldite® DY-K (from Huntsman), Polypox™ R6 (from Dow), Heloxy™ KR (from Hexion) or Erisys® GE-10 (from CVC Spec. Chem.).

The adduct is prepared preferably by slow metered addition of the epoxide to an initial charge of polyamine, the temperature of the reactants being maintained preferably in the range from 40 to 120° C., more particularly 50 to 110° C.

Preferred adducts are those of (i) at least one polyamine, having at least three amine hydrogens reactive toward epoxide groups, with (ii) at least one aromatic monoepoxide, these reactants being reacted in a molar ratio of approximately 1/1. During the reaction, the polyamine may have been present in excess and may have been removed by distillation after the reaction.

For an adduct of this kind, the polyamine is preferably selected from the group consisting of ethylenediamine, 1,2-propylenediamine, 1,3-propylenediamine, 1,4-butylenediamine, 1,3-butylenediamine, 1,2-butylenediamine, 2,3-butylenediamine, 2-methyl-1,3-propanediamine, DAMP, 2,2-dimethyl-1,3-propanediamine, 1,5-pentanediamine, MPMD, 1,6-hexanediamine, 2,5-dimethyl-1,6-hexanediamine, TMD, 1,2-diaminocyclohexane, 1,3-diaminocyclohexane, 1,4-diaminocyclohexane, IPDA, 2-methyl-1,3-diaminocyclohexane and 4-methyl-1,3-diaminocyclohexane, and mixtures thereof, 1,3-bis(amino-methyl)cyclohexane, 1,4-bis(aminomethyl)cyclohexane, 1,3-bis(aminomethyl) benzene, bis(2-aminoethyl) ether, 3,6-dioxaoctane-1,8-diamine, DETA, TETA, DPTA, N3-amine, N4-amine and BHMT.

For an adduct of this kind the aromatic monoepoxide is preferably a cresyl glycidyl ether.

Particularly preferred is an adduct of 1,2-propylenediamine with cresyl glycidyl ether that is prepared with an excess of 1,2-propylenediamine and with subsequent removal of the excess by distillation.

Further particularly preferred is an adduct of 1,5-diamino-2-methylpentane with cresyl glycidyl ether that has either been prepared with an excess of 1,5-diamino-2-methylpentane, with subsequent removal of the excess by distillation, or with a slight excess of cresyl glycidyl ether.

Further particularly preferred is an adduct of 2,2(4),4-trimethylhexamethylenediamine with cresyl glycidyl ether that is prepared with a slight excess of 2,2(4),4-trimethylhexamethylenediamine.

The term "excess" in the case of these particularly preferred adducts relates not to the reactive groups but rather to the molar ratio between the polyamine molecule and the cresyl glycidyl ether.

These particularly preferred adducts are of comparatively low viscosity, exhibit particularly high compatibility and reactivity with the customary epoxy resin compositions, have virtually no tendency toward blushing effects, and enable fully cured films of high gloss and high hardness to be produced.

Together with the amine of formula (I), particularly rapid development of strength in conjunction with good processability is achieved.

An especially preferred further amine is $N^1$-benzyl-1,2-propanediamine. A hardener which as well as the amine of the formula (I) comprises $N^1$-benzyl-1,2-propanediamine as further amine is of particular interest in particular because an amine of the formula (I) from reductive alkylation and $N^1$-benzyl-1,2-propanediamine can be prepared together in a simple way by carrying out reductive alkylation of 1,2-propylenediamine with a mixture of benzaldehyde and the aldehyde or ketone of the formula (II), especially salicylaldehyde. In this case a desired combination between low viscosity and high reactivity can be set through the selected ratio between $N^1$-benzyl-1,2-propanediamine and the amine of the formula (I).

Preference is given to a molar ratio between $N^1$-benzyl-1,2-propanediamine and the amine of the formula (I) in the range from 10/1 to 1/10, more particularly 5/1 to 1/5.

Particularly suitable as additive are accelerators, solvents, diluents, extenders, rheology modifiers or surface-active substances such as, in particular, wetting agents, flow control agents, deaerating agents or defoamers.

Suitable accelerators are substances which accelerate the reaction between amino groups and epoxide groups, more particularly acids or compounds which can be hydrolyzed to acids, more particularly organic carboxylic acids such as acetic acid, benzoic acid, salicylic acid, 2-nitrobenzoic acid, lactic acid, organic sulfonic acids such as methanesulfonic acid, p-toluenesulfonic acid or 4-dodecylbenzenesulfonic acid, sulfonic esters, other organic or inorganic acids such as, in particular, phosphoric acid, or mixtures of the aforementioned acids and acid esters; tertiary amines such as, in particular, 1,4-diazabicyclo[2.2.2]octane, benzyldimethylamine, α-methylbenzyldimethylamine, tri-ethanolamine, dimethylaminopropylamine, imidazoles such as, in particular, N-methylimidazole, N-vinylimidazole or 1,2-dimethylimidazole, salts of such tertiary amines, quaternary ammonium salts, such as, in particular benzyltrimethylammonium chloride, amidines such as, in particular, 1,8-diazabicyclo[5.4.0]undec-7-ene, guanidines such as, in particular, 1,1,3,3-tetramethylguanidine, phenols, especially bisphenols, phenolic resins or Mannich bases such as, in particular, 2-(dimethylaminomethyl)phenol, 2,4,6-tris(dimethylaminomethyl)phenol or polymers of phenol, formaldehyde and N,N-dimethyl-1,3-propanediamine, phosphites such as, in particular, diphenyl or triphenyl phosphites, or compounds containing mercapto groups. Preferred accelerators are acids, tertiary amines or Mannich bases.

Most preferred is salicylic acid or 2,4,6-tris(dimethylaminomethyl)phenol or a combination thereof.

The hardener preferably includes only a low level of accelerators, or none. As a result of the amine of the formula (I), the hardener is highly reactive even without additional accelerators. With preference the hardener, in particular, is largely free of 2,4,6-tris(dimethylaminomethyl)phenol, which in the hardener causes an unpleasant odor and emissions and may lead to yellowing of the cured composition. The hardener contains preferably less than 1 weight %, more preferably less than 0.5 weight %, more particularly less than 0.1 weight % of 2,4,6-tris(dimethylamino-methyl)phenol.

Suitability as solvents, diluents or extenders, referred to collectively below as diluents, is possessed more particularly by xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycol dibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycol di-n-butylyl ether, propylene glycol butyl ether, propylene glycol phenyl ether, dipropylene glycol, dipropylene glycol monomethyl ether, dipropylene glycol dimethyl ether, dipropylene glycol di-n-butyl ether, N-methylpyrrolidone, diphenylmethane, diisopropyl-naphthalene, petroleum fractions such as, in particular, Solvesso® grades (from Exxon), alkylphenols such as tert-butylphenol, nonylphenol, dodecylphenol and 8,11,14-pentadecatrienylphenol (cardanol, from cashew shell oil, available for example as Cardolite NC-700 from Cardolite Corp., USA), styrenized phenol, bisphenols, aromatic hydrocarbon resins, especially those containing phenol groups, alkoxylated phenol, especially ethoxylated or propoxylated phenol, more particularly 2-phenoxyethanol, adipates, sebacates, phthalates, benzoates, organic phosphoric acid esters or sulfonic acid esters or sulfonamides. Preferred are benzyl alcohol, dodecylphenol, tert-butylphenol, styrenized phenol, ethoxylated phenol, or aromatic hydrocarbon resins containing phenol groups, more particularly the Novares® grades LS 500, LX 200, LA 300 or LA 700 (from Rutgers).

The hardener preferably contains none or only a low level of diluents. With preference the hardener contains not more than 5 weight % of diluents.

Suitable rheology modifiers are, in particular, thickeners or antisettling agents.

The hardener may comprise further substances that are reactive toward epoxide groups, examples being monoamines such as hexylamine or benzylamine, or compounds containing mercapto groups, more particularly the following:

liquid, mercaptan-terminated polysulfide polymers, known under the brand name Thiokol® (from Morton Thiokol; available for example from SPI Supplies, or from Toray Fine Chemicals), more particularly types LP-3, LP-33, LP-980, LP-23, LP-55, LP-56, LP-12, LP-31, LP-32 or LP-2; and also, moreover, under the brand name Thioplast® (from Akzo Nobel), more particularly the types G 10, G 112, G 131, G 1, G 12, G 21, G 22, G 44 or G 4;

mercaptan-terminated polyoxyalkylene ethers, available for example by reaction of polyoxyalkylenediols or -triols either with epichlorohydrin or with an alkylene oxide, followed by sodium hydrogensulfide;

mercaptan-terminated compounds in the form of polyoxyalkylene derivatives known under the brand name Capcure® (from Cognis), especially types WR-8, LOF or 3-800;

polyesters of thiocarboxylic acids, for example pentaerythritol tetramercaptoacetate, trimethylolpropane trimercaptoacetate, glycol dimercaptoacetate, pentaerythritol tetra(3-mercaptopropionate), trimethylolpropane tri(3-mercaptopropionate) or glycol di-(3-mercaptopropionate), or products of esterification of polyoxyalkylenediols or -triols, of ethoxylated trimethylolpropane or of polyester diols with thiocarboxylic acids such as thioglycolic acid or 2- or 3-mercaptopropionic acid; or further compounds containing mercapto groups, such as, in particular, 2,4,6-trimercapto-1,3,5-triazine, 2,2'-(ethylenedioxy)diethanethiol (triethylene glycol dimercaptan) or ethanedithiol.

The hardener preferably comprises the amine of the formula (I) in an amount such that 1% to 95%, more preferably 5% to 90%, more particularly 10% to 80% of the amine hydrogens present in the hardener originate from the amine of the formula (I).

A further subject of the invention is an epoxy resin composition comprising a resin component comprising at least one epoxy resin, and a hardener component comprising at least one amine of the formula (I) as described above.

The hardener component is preferably a hardener comprising at least one amine of the formula (I) and at least one further amine and/or at least one additive, as described above.

Suitability as epoxy resin is possessed by customary technical epoxy resins. These are obtained in a known manner, as for example from the oxidation of the corresponding olefins or from the reaction of epichlorohydrin with the corresponding polyols, polyphenols or amines.

Particularly suitable as epoxy resin are what are called liquid polyepoxy resins, referred to hereinafter as "liquid resin". These have a glass transition temperature below 25° C.

Likewise possible as epoxy resin are what are called solid resins, which have a glass transition temperature above 25° C. and can be comminuted to powders which are pourable at 25° C.

Suitable epoxy resins are, in particular, aromatic epoxy resins, more particularly the glycidylization products of:

bisphenol A, bisphenol F or bisphenol A/F, where A stands for acetone and F for formaldehyde, which served as reactants in the preparation of these bisphenols. In the case of bisphenol F, there may also be positional isomers present, derived more particularly from 2,4'- or 2,2'-hydroxyphenylmethane.

dihydroxybenzene derivatives such as resorcinol, hydroquinone or pyrocatechol;

further bisphenols or polyphenols such as bis(4-hydroxy-3-methylphenyl)methane, 2,2-bis(4-hydroxy-3-methylphenyl)propane (bisphenol C), bis(3,5-dimethyl-4-hydroxyphenyl)methane, 2,2-bis(3,5-dimethyl-4-hydroxyphenyl)propane, 2,2-bis(3,5-dibromo-4-hydroxy-phenyl)propane, 2,2-bis(4-hydroxy-3-tert-butyl-phenyl)propane, 2,2-bis(4-hydroxyphenyl) butane (bisphenol B), 3,3-bis(4-hydroxyphenyl) pentane, 3,4-bis(4-hydroxyphenyl)hexane, 4,4-bis(4-hydroxyphenyl)-heptane, 2,4-bis(4-hydroxyphenyl)-2-methylbutane, 2,4-bis(3,5-dimethyl-4-hydroxyphenyl)-2-methylbutane, 1,1-bis(4-hydroxyphenyl) cyclohexane (bisphenol Z), 1,1-bis(4-hydroxyphenyl)-3,3,5-trimethylcyclohexane (bisphenol-TMC), 1,1-bis (4-hydroxyphenyl)-1-phenyl-ethane, 1,4-bis[2-(4-hydroxyphenyl)-2-propyl]benzene (bisphenol P), 1,3-bis[2-(4-hydroxyphenyl)-2-propyl]-benzene (bisphenol M), 4,4'-dihydroxybiphenyl (DOD), 4,4'-dihydroxybenzophenone, bis(2-hydroxynaphth-1-yl) methane, bis(4-hydroxynaphth-1-yl)methane, 1,5-dihydroxynaphthalene, tris(4-hydroxyphenyl)methane, 1,1,2,2-tetrakis(4-hydroxyphenyl)ethane, bis(4-hydroxyphenyl) ether or bis(4-hydroxyphenyl) sulfone;

condensation products of phenols with formaldehyde which are obtained under acidic conditions, such as phenol novolaks or cresol novolaks, also called bisphenol F novolaks;

aromatic amines, such as aniline, toluidine, 4-aminophenol, 4,4'-methylenediphenyldiamine, 4,4'-methylenediphenyldi-(N-methyl)amine, 4,4'-[1,4-phenylenebis(l-methylethylidene)]bisaniline (bisaniline P) or 4,4'-[1,3-phenylenebis(l-methylethylidene)]bisaniline (bisaniline M).

Further suitable epoxy resins are aliphatic or cycloaliphatic polyepoxides, more particularly glycidyl ethers of saturated or unsaturated, branched or unbranched, cyclic or open-chain di-, tri- or tetrafunctional $C_2$ to $C_{30}$ alcohols, especially ethylene glycol, propylene glycol, butylene glycol, hexanediol, octanediol, polypropylene glycols, dimethylolcyclohexane, neopentyl glycol, dibromoneo-pentyl glycol, castor oil, trimethylolpropane, tri-methylolethane, pentaerythritol, sorbitol or glycerol, or alkoxylated glycerol or alkoxylated trimethylolpropane;

a hydrogenated bisphenol A, F or A/F liquid resin, or the glycidylization products of hydrogenated bisphenol A, F or A/F;

an N-glycidyl derivative of amides or heterocyclic nitrogen bases, such as triglycidyl cyanurate or triglycidyl isocyanurate, or reaction products of epichlorohydrin with hydantoin.

epoxy resins from the oxidation of olefins, such as, in particular, vinylcyclohexene, dicyclopentadiene, cyclohexadiene, cyclododecadiene, cyclododecatriene, isoprene, 1,5-hexadiene, butadiene, polybutadiene or divinylbenzene.

A preferred epoxy resin in the resin component is a liquid resin based on a bisphenol, more particularly a diglycidyl ether of bisphenol A, bisphenol F or bisphenol A/F, of the kind available commercially, for example, from Dow, Huntsman or Momentive. These liquid resins have a low viscosity for epoxy resins and in the cured state exhibit good properties as a coating. They may include fractions of solid bisphenol A resin or bisphenol F novolaks.

The resin component may comprise a reactive diluent, more particularly a reactive diluent having at least one epoxide group. Particularly suitable as reactive diluents are the glycidyl ethers of mono- or polyhydric phenols or aliphatic or cycloaliphatic alcohols, such as, in particular, the aforementioned polyglycidyl ethers of di- or polyols, or, furthermore, phenyl glycidyl ether, cresyl glycidyl ether, benzyl glycidyl ether, p-n-butylphenyl glycidyl ether, p-tert-butylphenyl glycidyl ether, nonylphenyl glycidyl ether, allyl glycidyl ether, butyl glycidyl ether, hexyl glycidyl ether, 2-ethylhexyl glycidyl ether, or glycidyl ethers of natural alcohols such as, in particular, $C_8$ to $C_{10}$ alkyl glycidyl ether or $C_{12}$ to $C_{14}$ alkyl glycidyl ether. The addition of a reactive diluent to the epoxy resin has the effect of reducing the viscosity, and/or of reducing the glass transition temperature and/or the mechanical values.

The epoxy resin composition optionally comprises further constituents, particularly auxiliaries and adjuvants customarily used in epoxy resin compositions, examples being the following:

solvents, diluents, or extenders, such as especially the aforementioned diluents;

reactive diluents, especially reactive diluents containing epoxide groups, as mentioned above, epoxidized soybean oil or linseed oil, compounds containing acetoacetate groups, especially acetoacetylated polyols, butyrolactone, carbonates, aldehydes, and also, moreover, isocyanates or silicones containing reactive groups;

polymers, especially polyamides, polysulfides, polyvinylformal (PVF), polyvinylbutyral (PVB), polyurethanes (PU), polymers with carboxyl groups, polyamides, butadiene-acrylonitrile copolymers, styrene-acrylonitrile copolymers, butadiene-styrene copolymers, homo- or copolymers of unsaturated monomers, especially from the group encompassing ethylene, propylene, butylene, isobutylene, isoprene, vinyl acetate or alkyl (meth)acrylates, especially chlorosulfonated polyethylenes or fluorine-containing polymers, sulfonamide-modified melamines or purified Montan waxes;

inorganic or organic fillers, especially ground or precipitated calcium carbonates, with or without a coating of fatty acids, more particularly of stearates, barytes (heavy spar), talcs, finely ground quartzes, silica sand, iron mica, dolomites, wollastonites, kaolins, mica (potassium aluminum silicate), molecular sieves, aluminum oxides, aluminum hydroxides, magnesium hydroxide, silicas, cements, gypsums, flyashes, carbon black, graphite, metal powders such as aluminum, copper, iron, zinc, silver or steel, PVC powders or hollow beads;

fibers, especially glass fibers, carbon fibers, metal fibers, ceramic fibers, or polymeric fibers such as polyamide fibers or polyethylene fibers;

pigments, especially titanium dioxide and/or iron oxides;

the aforementioned accelerators;

rheology modifiers, especially thickeners or antisettling agents;

adhesion promoters, especially organoalkoxysilanes;

stabilizers against oxidation, heat, light or UV radiation;

flame retardants, especially aluminum hydroxide (ATH), magnesium dihydroxide (MDH), antimony trioxide, antimony pentoxide, boric acid $(B(OH)_3)$, zinc borate, zinc phosphate, melamine borate, melamine cyanurate, ammonium polyphosphate, melamine phosphate, melamine pyrophosphate, polybrominated diphenyl oxides or diphenyl ethers, phosphates such as especially diphenyl cresyl phosphate, resorcinol bis(diphenyl phosphate), resorcinol diphosphate oligomer, tetraphenylresorcinol diphosphite, ethylenediamine diphosphate or bisphenol A bis(diphenyl phosphate), tris(chloroethyl) phosphate, tris(chloropropyl) phosphate or tris(dichloro-isopropyl) phosphate, tris[3-bromo-2,2-bis(bromo-methyl)propyl] phosphate, tetrabromobisphenol A, bis(2,3-dibromopropyl ether) of bisphenol A, brominated epoxy resins, ethylenebis(tetrabromo-phthalimide), ethylenebis(dibromonorbornanedicarboximide), 1,2-bis-(tribromophenoxy)ethane, tris(2,3-dibromopropyl) isocyanurate, tribromophenol, hexabromocyclododecane, bis(hexachlorocyclopentadieno)cyclooctane or chlorinated paraffins;

surface-active substances, especially wetting agents, flow control agents, deaerating agents or defoamers;

biocides, such as, for example, algicides, fungicides or fungal growth inhibitors.

The epoxy resin composition preferably comprises further auxiliaries and adjuvants, especially wetting agents, flow control agents, defoamers, stabilizers, pigments and/or accelerators.

The epoxy resin composition preferably contains none or only a small amount of diluents, preferably not more than 5 weight %, especially not more than 2 weight %.

The ratio of the number of groups that are reactive toward epoxide groups in the epoxy resin composition, to the number of epoxide groups, is preferably in the range from 0.5 to 1.5, more particularly 0.7 to 1.2.

The amine hydrogens and, where present, other groups that are reactive toward epoxide groups, present in the epoxy resin composition, react with the epoxide groups with ring-opening of the latter groups (addition reaction). As a result of these reactions, the composition undergoes polymerization and ultimately cures. The person skilled in the art is aware that primary amino groups are difunctional groups with respect to epoxide groups, and a primary amino group therefore counts as two groups that are reactive toward epoxide groups.

The two components of the epoxy resin composition are each stored in their own container. Further constituents of the epoxy resin composition may be present as part of the resin component or of the hardener component, with further constituents that are reactive toward epoxide groups preferably being part of the hardener component. A suitable container for storing the resin component or the hardener component is, in particular, a drum, a hobbock, a pouch, a pail, a canister, a cartridge or a tube. The components are storable, meaning that they can be kept for several months up to a year or more before being employed, without suffering alteration in their respective properties to any extent relevant for their use. For the use of the epoxy resin composition, the resin component and the hardener component are mixed with one another shortly before or during application. The mixing ratio between the two components is preferably selected such that the groups of the hardener component that are reactive toward epoxide groups are present in an appropriate ratio to the epoxide groups of the resin component, as described above. In terms of parts by weight, the mixing ratio between the resin component and the hardener component is customarily in the range from 1:10 to 10:1.

The two components are mixed by means of suitable method; this may take place continuously or batchwise. If mixing takes place prior to application, it should be ensured that not too much time elapses between the mixing of the components and application, since otherwise there may be disruptions, such as retarded or incomplete development of adhesion to the substrate, for example. Mixing takes place in particular at ambient temperature, which is typically in the range from about 5 to 50° C., preferably at about 10 to 30° C.

The mixing of the two components is at the same time the start of curing through chemical reaction, as described above. Curing takes place in particular at ambient temperature. It typically extends over several days to weeks, until it has largely concluded under the prevailing conditions. The duration is dependent on factors including the temperature, the reactivity of the constituents and their stoichiometry, and also the presence of accelerators.

A cured epoxy resin composition is obtained from the curing of the composition.

The epoxy resin composition is applied to at least one substrate, those below being particularly suitable:

glass, glass-ceramic, concrete, mortar, brick, tile, plaster or natural stones such as granite or marble;

metals or alloys such as aluminum, iron, steel or nonferrous metals, or surface-enhanced metals or alloys such as galvanized or chromed metals;

leather, textiles, paper, wood, woodbase materials bonded with resins, such as phenolic, melamine or epoxy resins, for example, resin-textile composites, or other polymer composites;

plastics, especially rigid or flexible PVC, ABS, polycarbonate (PC), polyamide (PA), polyesters, PMMA, epoxy resins, PU, POM, PO, PE, PP, EPM or EPDM, the plastics having optionally been surface-treated by plasma, corona or flame treatment;

fiber-reinforced plastics, such as carbon fiber-reinforced plastics (CRP), glass fiber-reinforced plastics (GRP) or sheet molding compounds (SMC);

coated substrates, such as powder-coated metals or alloys; paints or varnishes.

As and when necessary, the substrates may be pretreated before the epoxy resin composition is applied. Such pretreatments include, in particular, physical and/or chemical cleaning techniques, as for example sanding, sandblasting, shotblasting, brushing and/or blowing, and also, furthermore, treatment with cleaners or solvents, or the application of an adhesion promoter, an adhesion promoter solution or a primer.

The epoxy resin composition described can be used with advantage as a fiber composite matrix for fiber composite materials (composites) such as, in particular, CRP or GRP, or as an encapsulating compound, sealant, adhesive, covering, coating, paint, varnish, seal, priming coat or primer, and also as a cementitious product such as, in particular, repair mortar or grout.

More particularly it can be used as an encapsulating compound, such as an electrical encapsulant, for example, or as an adhesive, more particularly as a bodywork adhesive, sandwich element adhesive, half-shell adhesive for rotor blades of wind turbines, bridge element adhesive or anchoring adhesive.

It can also be used, in particular, as a covering, coating, paint, varnish, seal, priming coat or primer for construction and industry applications, more particularly as a floor covering or floor coating for interiors such as offices, industrial halls, sports halls or cooling rooms, or, in the exterior segment, for balconies, terraces, parking decks, bridges or roofs, as a protective coating for concrete, cement, metals, plastics or wood, for the surface sealing of wooden constructions, vehicles, loading areas, tanks, silos, shafts, piping circuits, pipelines, machines or steel constructions, for example, such as of boats, piers, offshore platforms, sluice gates, hydroelectric power stations, river constructions, swimming pools, wind turbines, bridges, chimneys, cranes or sheet-pile walls, for example.

In particular, moreover, it can be used as an undercoat, tie coat, anticorrosion primer, or for rendering surfaces hydrophobic.

The fully or partly cured epoxy resin composition, especially when used as a coating, covering or paint, may have a further coating, covering or paint applied to it, in which case this further layer may likewise comprise an epoxy resin composition, or else may comprise a different material, particularly a polyurethane coating or polyurea coating.

With particular advantage the epoxy resin composition described is used as a coating.

A further subject of the invention, accordingly, is a coating comprising an epoxy resin composition as described above.

A coating in this context refers to two-dimensionally applied coverings of all kinds, especially paints, varnishes, seals, priming coats or primers, as described above, or floor coverings or protective coatings, including in particular those for heavy-duty corrosion control.

With particular advantage the epoxy resin composition described is used in low-emission coatings that carry eco-quality seals, according for example to Emicode (EC1 Plus), AgBB, DIBt, Der Blaue Engel, AFSSET, RTS (M1), and US Green Building Council (LEED).

As a coating, the epoxy resin composition is used advantageously in a method for coating, where it has a liquid consistency with low viscosity and good leveling properties and is applied more particularly as a self-leveling or thixotrope coating to predominantly planar surfaces or as a paint. In the context of this application, the viscosity of the epoxy resin composition immediately after the mixing of the resin and hardener components, and as measured at 20° C., is preferably in the range from 300 to 10,000 mPa·s, preferably in the range from 300 to 7,500 mPa·s, more preferably in the range from 300 to 4000 mPa·s especially in the range from 300 to 2000 mPa·s, most preferably in the range from 700 to 1000 mPa·s. Within the working time, the mixed composition is applied two-dimensionally as a thin film having a layer thickness of typically about 50 □m to about 5 mm to a substrate, typically at ambient temperature. Application is accomplished in particular by pouring the composition onto the substrate that is to be coated, and then spreading it evenly with the aid, for example, of a doctor blade or toothed applicator. Application may alternatively take place with a brush or roller or by spray application, as an anticorrosion coating on steel, for example.

Curing is typically accompanied by the development of largely clear, glossy and nonsticky films of high-hardness, which exhibit effective adhesion to a very wide variety of substrates.

The films are particularly stable with respect to moisture and various chemicals, a quality promoted by the phenol groups incorporated into the matrix.

The use of the epoxy resin composition results in an article comprising the cured compositions described.

The epoxy resin composition described is notable for advantageous properties. It is phenol-free and can be processed well even without diluents. It cures even without accelerator both at room temperature and at lower ambient temperatures very rapidly, and in so doing develops high hardness and an attractive surface, with virtually no yellowing.

A further subject of the invention is a method for accelerating the curing of an epoxy resin composition by adding an amine of the formula (I) as described above.

The epoxy resin composition here comprises, in particular, a resin component and a hardener component or hardener. The amine of the formula (I) is preferably added to the hardener component or hardener. The hardener preferably comprises at least one amine such as the further amines identified above, more particularly at least one of the preferred amines identified above.

The amine of formula (I) is preferably added in an amount such that 1% to 80%, more particularly 2% to 50%, more particularly 3% to 30%, of the amine hydrogens present in the hardener originate from the amine of the formula (I).

EXAMPLES

Set out below are working examples which are intended to elucidate in more detail the invention described. The invention is of course not confined to these working examples described.

"AHEW" stands for the amine hydrogen equivalent weight.

"EEW" stands for the epoxide equivalent weight.

"Standard conditions" refer to a temperature of 23±1° C. and a relative atmospheric humidity of 50±5%. "SC" stands for "standard conditions".

Description of Measurement Methods:

Infrared spectra (FT-IR) were measured as undiluted films on an FT-IR instrument 1600 from Perkin-Elmer equipped with a horizontal ATR measurement unit with ZnSe crystal; the absorption bands are reported in wavenumbers ($cm^{-1}$); (measuring window: 4000-650 $cm^{-1}$).

The viscosity was measured on a thermostated cone/plate viscometer, Rheotec RC30 (cone diameter 50 mm, cone angle 1°, cone tip/plate distance 0.05 mm, shear rate 10 $s^{-1}$).

The amine number was determined by titration (with 0.1N $HClO_4$ in acetic acid against crystal violet).

Preparation of Amines of the Formula (I)

Amine A1: Reaction Product Comprising $N^1$-(2-hydroxybenzyl)-1,2-propanediamine A round-bottomed flask was charged at room temperature with 92.67 g (1.25 mol) of 1,2-propylenediamine under a nitrogen atmosphere. With thorough stirring, a solution of 30.53 g (0.25 mol) salicylaldehyde in 800 ml of isopropanol was added slowly dropwise, followed by stirring for 2 hours more. Thereafter the reaction mixture was hydrogenated under a hydrogen pressure of 90 bar, at a temperature of 95° C. and with a flow rate of 4 ml/min, on a continuous hydrogenation apparatus with Pd/C fixed-bed catalyst. To monitor the reaction, IR spectroscopy was used to verify whether the imine band at about 1665 cm had disappeared. At that point the hydrogenated solution was concentrated under reduced pressure at 65° C. This gave a yellowish liquid having a viscosity of 5.2 Pas at 20° C. and an amine number of 573 mg KOH/g.

FT-IR: 3286, 3044, 2958, 2921, 2850, 2725, 2588, 1589, 1455, 1412, 1378, 1253, 1184, 1150, 1102, 1035, 931, 842, 772.

Amine A2: Reaction Product Comprising $N^1$-(2-hydroxybenzyl)-1,2-propanediamine and $N^1$-benzyl-1,2-propanediamine A round-bottomed flask was charged at room temperature with 92.67 g (1.25 mol) of 1,2-propylenediamine under a nitrogen atmosphere. With thorough stirring, a solution of 6.10 g (0.05 mol) salicylaldehyde and 21.22 g (0.20 mol) of benzaldehyde in 500 ml of isopropanol was added slowly dropwise, followed by stirring for 2 hours more. Thereafter the reaction mixture was hydrogenated under a hydrogen pressure of 85 bar, at a temperature of 95° C. and with a flow rate of 5 ml/min, on a continuous hydrogenation apparatus with Pd/C fixed-bed catalyst. To monitor the reaction, IR spectroscopy was used to verify whether the imine band at about 1665 $cm^{-1}$ had disappeared. At that point the hydrogenated solution was concentrated under reduced pressure at 65° C. This gave a yellow liquid having a viscosity of 0.1 Pas at 20° C. and an amine number of 630 mg KOH/g.

FT-IR: 3025, 2957, 2820, 1590, 1493, 1452, 1373, 1256, 1105, 1027, 828, 733, 699.

Amine A3: Reaction Product Comprising 2,4,6-tris(((2-aminopropyl)amino)methyl)phenol A round-bottomed flask with reflux condenser (cooling water temperature 12° C.) was charged with 148.26 g (2.00 mol) of 1,2-propylenediamine and 43.8 g (0.17 mol) of 2,4,6-tris(dimethylaminomethyl)phenol (Ancamine® K 54, from Air Products) under a nitrogen atmosphere and this initial charge was heated to 130° C. Over 5 hours, the temperature was maintained and 1,2-propylenediamine was refluxed, while dimethylamine liberated was collected in a cold trap downstream of the reflux condenser. The reaction mixture was subsequently concentrated under reduced pressure at 65° C. This gave a yellowish liquid having a viscosity of 82.3 Pas at 40° C. and an amine number of 933 mg KOH/g.

FT-IR: 3285, 2954, 2813, 1608, 1450, 1405, 1356, 1294, 1250, 1175, 1146, 1103, 1026, 988, 875.

Amine A4: Reaction Product Comprising 2,4,6-tris(((2-aminopropyl)amino)methyl)phenol A round-bottomed flask with reflux condenser (cooling water temperature 12° C.) was charged with 25.94 g (0.35 mol) of 1,2-propylenediamine and 29.49 g (0.11 mol) of 2,4,6-tris(dimethylaminomethyl)phenol (Ancamine® K 54, from Air Products) under a nitrogen atmosphere and this initial charge was heated to 135° C. Over 5 hours, the temperature was maintained and 1,2-propylenediamine was refluxed, while dimethylamine liberated was collected in a cold trap downstream of the reflux condenser. The reaction mixture was subsequently concentrated under reduced pressure at 65° C. This gave a yellowish liquid having a viscosity of 3.9 Pas at 40° C. and an amine number of 865 mg KOH/g.

FT-IR: 3275, 2955, 2816, 1607, 1455, 1371, 1294, 1250, 1147, 1105, 837, 787.

Preparation of Amines for Comparison Purposes

Amine C1: Reaction Product Comprising $N^1$-benzyl-1,2-propanediamine

A round-bottomed flask was charged at room temperature with 22.1 g (0.3 mol) of 1,2-propylenediamine under a nitrogen atmosphere. With thorough stirring, a solution of 31.8 g (0.3 mol) benzaldehyde in 500 ml of isopropanol was added slowly dropwise, followed by stirring for 30 minutes more. Thereafter the reaction mixture was hydrogenated under a hydrogen pressure of 85 bar, at a temperature of 85° C. and with a flow rate of 5 ml/min, on a continuous hydrogenation apparatus with Pd/C fixed-bed catalyst. To monitor the reaction, IR spectroscopy was used to verify whether the imine band at about 1665 cm had disappeared. At that point the hydrogenated solution was concentrated under reduced pressure at 65° C. This gave a yellowish liquid having a viscosity of 19 mPa·s at 20° C. and an amine number of 574 mg KOH/g.

FT-IR: 3026, 2956, 2818, 1601, 1494, 1452, 1373, 1115, 1073, 1028, 826, 732, 696.

Amine C2: Reaction Product Comprising $N^1$-(2-hydroxybenzyl)-4-methyl-1,5-pentanediamine A round-bottomed flask was charged at room temperature with 23.24 g (0.20 mol) of 1,5-diamino-2-methylpentane (Dytek® A, from Invista) under a nitrogen atmosphere. With thorough stirring, a solution of 24.42 g (0.20 mol) salicylaldehyde in 250 ml of isopropanol was added slowly dropwise, followed by stirring for 2 hours more. Thereafter the reaction mixture was hydrogenated under a hydrogen pressure of 80 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a yellow liquid having a viscosity of 2.3 Pas at 20° C. and an amine number of 506 mg KOH/g.

FT-IR: 2924, 2850, 1589, 1455, 1411, 1255, 1101, 930, 842, 748, 719.

Amine C3: Reaction Product Comprising N$^1$-(2-hydroxybenzyl)-3,3(5),5-trimethyl-1,6-hexanediamine A round-bottomed flask was charged at room temperature with 15.82 g (0.10 mol) of 2,2(4),4-trimethylhexamethylenediamine (Vestamin® TMD, from Evonik) under a nitrogen atmosphere. With thorough stirring, a solution of 12.21 g (0.10 mol) salicylaldehyde in 250 ml of isopropanol was added slowly dropwise, followed by stirring for 2 hours more. Thereafter the reaction mixture was hydrogenated under a hydrogen pressure of 80 bar, at a temperature of 90° C. and with a flow rate of 4 ml/min, on a continuous hydrogenation apparatus with Pd/C fixed-bed catalyst. To monitor the reaction, IR spectroscopy was used to verify whether the imine band at about 1665 cm$^{-1}$ had disappeared. At that point the hydrogenated solution was concentrated under reduced pressure at 65° C. This gave a dark-yellow liquid having a viscosity of 4.4 Pa-s at 20° C. and an amine number of 414 mg KOH/g.

FT-IR: 3045, 2952, 2912, 2868, 1589, 1470, 1256, 1101, 931, 844, 748, 720.

Amine C4: Reaction Product Comprising N-(2-hydroxybenzyl)-1,3-bis(aminomethyl)benzene A round-bottomed flask was charged at room temperature with 27.24 g (0.20 mol) of 1,3-bis(aminomethyl)benzene (MXDA, from Mitsubishi Gas Chemicals) under a nitrogen atmosphere. With thorough stirring, a solution of 24.42 g (0.20 mol) salicylaldehyde in 250 ml of isopropanol was added slowly dropwise, followed by stirring for 2 hours more. Thereafter the reaction mixture was hydrogenated under a hydrogen pressure of 80 bar, at a temperature of 90° C. and with a flow rate of 5 ml/min, on a continuous hydrogenation apparatus with Pd/C fixed-bed catalyst. To monitor the reaction, IR spectroscopy was used to verify whether the imine band at about 1665 cm had disappeared. At that point the hydrogenated solution was concentrated under reduced pressure at 65° C. This gave a yellowish liquid having a viscosity of 22.3 Pa-s at 20° C. and an amine number of 463 mg KOH/g.

FT-IR: 3022, 2846, 2721, 2613, 1587, 1454, 1254, 1082, 843, 747, 699.

Amine C5: Reaction Product Comprising N$^1$-(2-hydroxybenzyl)-4,7-diaza-,10-decanediamine A round-bottomed flask was charged at room temperature with 34.85 g (0.20 mol) of N,N'-bis(3-aminopropyl)-ethylenediamine (N4-Amine, from BASF) under a nitrogen atmosphere. With thorough stirring, a solution of 24.42 g (0.20 mol) salicylaldehyde in 400 ml of isopropanol was added slowly dropwise, followed by stirring for 2 hours more. Thereafter the reaction mixture was hydrogenated under a hydrogen pressure of 85 bar, at a temperature of 90° C. and with a flow rate of 4 ml/min, on a continuous hydrogenation apparatus with Pd/C fixed-bed catalyst. To monitor the reaction, IR spectroscopy was used to verify whether the imine band at about 1665 cm had disappeared. At that point the hydrogenated solution was concentrated under reduced pressure at 65° C. This gave a yellowish liquid having a viscosity of 2.5 Pas at 20° C. and an amine number of 794 mg KOH/g.

FT-IR: 3287, 2927, 2837, 1630, 1581, 1496, 1458, 1277, 1150, 1115, 953, 836, 746, 736.

Production of Hardeners and Epoxy Resin Compositions

For each example, the ingredients specified in tables 1 to 2 were mixed in the stated quantities (in parts by weight) of the hardener component using a centrifugal mixer (SpeedMixer™ DAC 150, FlackTek Inc.) and the mixtures were stored in the absence of moisture.

Similarly, the ingredients of the resin component as specified in tables 1 to 2 were processed and stored.

Thereafter the two components of each composition were processed to a homogeneous liquid using the centrifugal mixer, and this liquid was tested immediately as follows:

10 minutes after mixing, the viscosity at 20° C. was ascertained ("Viscosity (10')").

A first film was drawn down in a film thickness of 500 μm onto a glass plate, which was stored/cured under standard conditions. Determined on this film was the König hardness (pendulum hardness as per König, measured to DIN EN ISO 1522) after 1 day ("König hardness (1 d SC)"), after 2 days ("König hardness (2 d SC)"), after 4 days ("König hardness (4 d SC)"), after 7 days ("König hardness (7 d SC)"), and after 14 days ("König hardness (14 d SC)"). After 14 days, the appearance of the film was assessed (identified in the table as "appearance (SC)". A film identified as "attractive" there was clear and had a glossy and nonsticky surface without structure. "Structure" here refers to any kind of marking or pattern on the surface.

A second film was drawn down onto a glass plate in a film thickness of 500 μm, and this film immediately after application was stored, or cured, at 8° C. and at 80% relative humidity for 7 days and subsequently under standard conditions (SC) for 3 weeks. Thereafter the appearance of this film was assessed (identified in the tables as "appearance (8°/80%)"), in the same way as described for the appearance (SC). On the films cured in this way, the König hardness was again determined, in each case after 7 days at 8° C. and 80% relative humidity ("König hardness (7 d 8°/80%)"), then after a further 2 days under SC ("König hardness (7 d 8°/80%) (+2 d SC)") and 7 days under SC ("König hardness (7 d 8°/80%) (+7 d SC)").

The measure used for the yellowing, moreover, was the color change after exposure in a weathering tester. For this purpose, a further film was drawn down in a film thickness of 500 μm onto a glass plate and was stored, or cured, under standard conditions for 2 weeks and subsequently exposed in a Q-Sun Xenon Xe-1 weathering tester with Q-SUN Daylight-Q optical filter and with a xenon lamp, with a luminous intensity of 0.51 W/m$^2$ at 340 nm and at a temperature of 65° C. for 72 hours (Q-Sun (72 h)). Thereafter the color difference ΔE of the film thus exposed was determined in comparison to the corresponding unexposed film, using an NH310 colorimeter from Shenzen 3NH Technology Co. LTD, equipped with Silicon Photoelectric Diode Detector, Light Source A, Color Space Measurement Interface CIE L*a*b*C*H*. A high ΔE value here represents a large color difference, and severe yellowing.

The results are reported in tables 1 to 2.

The epoxy resin compositions EZ-1 to EZ-4 are inventive examples. The epoxy resin compositions Ref-1 to Ref-5 are comparative examples.

Substances Used:

Araldite® GY 250: bisphenol A diglycidyl ether, EEW about 187.5 g/eq (from Huntsman)

Araldite® DY-E: monoglycidyl ether of $C_{12}$ to $C_{14}$ alcohols, EEW about 290 g/eq (from Huntsman)

TABLE 1

Composition and properties of EZ-1 to EZ-4 and Ref-1.

| Compositions | | EZ-1 | EZ-2 | EZ-3 | EZ-4 | Ref-1 |
|---|---|---|---|---|---|---|
| Resin comp.: | | | | | | |
| Araldite ® GY-250 | | 167.2 | 167.2 | 167.2 | 167.2 | 167.2 |
| Araldite ® DY-E | | 31.8 | 31.8 | 31.8 | 31.8 | 31.8 |
| Hardener comp.: | | | | | | |
| Amine A1 | | 60.1 | — | — | — | — |
| Amine A2 | | — | — | — | 55.1 | — |
| Amine A3 | | — | 39.2 | — | — | — |
| Amine A4 | | — | — | 39.2 | — | — |
| Amine C1 | | — | — | — | — | 54.7 |
| Viscosity (10') [Pa · s] | | 1.75 | 7.43 | 2.93 | 0.56 | 0.46 |
| König hardness | (1 d SC) | 84 | 85 | 94 | 52 | 5 |
| [s] | (2 d SC) | 147 | 104 | 108 | 126 | 25 |
| | (4 d SC) | 171 | 129 | 120 | 165 | 40 |
| | (7 d SC) | 195 | 148 | 126 | 193 | 73 |
| | (14 d SC) | 207 | 171 | 150 | 210 | 75 |
| Appearance (SC) | | attractive, colorless | attractive, colorless | Slightly cloudy, colorless | attractive, colorless | attractive, colorless |
| König hardness | (7 d 8°/80%) | 65 | 56 | 27 | 46 | 12 |
| [s] | (+2 d SC) | 168 | 85 | 36 | 157 | 25 |
| | (+7 d SC) | 203 | 111 | 39 | 197 | 39 |
| Appearance (8°/80%) | | attractive, colorless | matt, slight texture, colorless | matt, slightly cloudy, colorless | attractive, colorless | attractive, colorless |

TABLE 2

Composition and properties of EZ-1 and Ref-2 to Ref-5.

| Example | | EZ-1 | Ref-2 | Ref-3 | Ref-4 | Ref-5 |
|---|---|---|---|---|---|---|
| Resin comp.: | | | | | | |
| Araldite ® GY-250 | | 167.2 | 167.2 | 167.2 | 167.2 | 167.2 |
| Araldite ® DY-E | | 31.8 | 31.8 | 31.8 | 31.8 | 31.8 |
| Hardener comp.: | | | | | | |
| Amine A1 | | 60.1 | — | — | — | — |
| Amine C2 | | — | 74.1 | — | — | — |
| Amine C3 | | — | — | 88.1 | — | — |
| Amine C4 | | — | — | — | 80.8 | — |
| Amine C5 | | — | — | — | — | 56.1 |
| Viscosity (10') [Pa · s] | | 1.75 | 1.68 | 2.37 | 3.78 | 2.63 |
| König hardness | (1 d SC) | 84 | 60 | 31 | 150 | 74 |
| [s] | (2 d SC) | 147 | 108 | 71 | 182 | 87 |
| | (4 d SC) | 171 | 138 | 110 | 184 | 87 |
| | (7 d SC) | 195 | 155 | 153 | 193 | 95 |
| | (14 d SC) | 207 | 189 | 175 | 208 | 102 |
| Appearance (SC) | | attractive, colorless | slight texture, yellowish | attractive, yellowish | slight texture, yellowish | sticky, matt, yellowish |
| Q-Sun (72 h) ΔE | | 3.8 | 12.3 | 5.7 | 5.8 | 6.1 |
| König hardness | (7 d 8°/80%) | 65 | 27 | 33 | 119 | 52 |
| [s] | (+2 d SC) | 168 | 45 | 95 | 171 | 95 |
| | (+7 d SC) | 203 | 103 | 153 | 185 | 113 |
| Appearance (8°/80%) | | attractive, colorless | matt, slight texture, yellowish | slightly matt, yellowish | matt, slight texture, yellowish | cloudy, sticky, texture, yellowish |

The invention claimed is:
1. An amine of the formula (I),

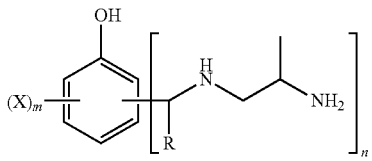

where
m is 0 or 1 or 2,
n is 1 or 2 or 3,
R is a hydrogen radical or alkyl radical having 1 to 8 carbon atoms or phenyl radical, and
X represents identical or different radicals selected from the group consisting of hydroxyl, alkyl, alkenyl and alkoxy, N-pyrrolidinylmethyl, N-piperidinylmethyl, and N-morpholiynlmethyl, wherein each of said alkyl, alkenyl and alkoxy has up to 18 carbon atoms and optionally contains ether oxygen, hydroxyl oxygen or amine nitrogen.

2. The amine as claimed in claim 1, wherein m is 0 or 1, n is 1, and R is a hydrogen radical or methyl radical.

3. The amine as claimed in claim 1, wherein (m+n) is 3, R is a hydrogen radical, and X is an N,N-dialkyl radical which optionally contains one or two hydroxyl groups, or is an N-alkyl radical which optionally contains a hydroxyl group or one or two amine nitrogens, or is an N-pyrrolidinylmethyl or N-piperidinylmethyl or N-morpholinylmethyl radical.

4. A process for preparing the amine as claimed in claim 1, wherein 1,2-propylenediamine is reacted
either, with reductive alkylation, with at least one aldehyde or ketone of the formula (II) and hydrogen

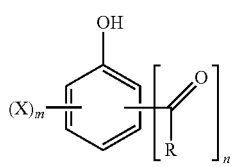

or, with transamination, with a Mannich base of the formula (III)

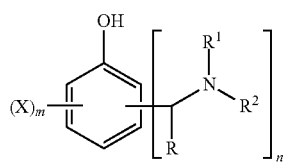

where
$R^1$ and $R^2$ are each identical or different alkyl, cycloalkyl or aralkyl radicals having 1 to 4 carbon atoms and optionally containing ether oxygen or amine nitrogen, or together are an alkylene radical having 4 to 8 carbon atoms and optionally containing ether oxygen or amine nitrogen.

5. The process as claimed in claim 4, wherein it is carried out with a ratio between the number of 1,2-propylenediamine molecules and the number of aldehyde or keto groups in the aldehyde or ketone of the formula (II) of at least 1.5/1.

6. The process as claimed in claim 4, wherein it is carried out with salicylaldehyde or 2'-hydroxyacetophenone as aldehyde or ketone of the formula (II).

7. The process as claimed in claim 4, wherein it is carried out with a ratio between the number of 1,2-propylenediamine molecules and the number of aminoalkyl substituents in the Mannich base of the formula (III) of at least 1/1.

8. The process as claimed in claim 4, wherein it is carried out with 2,4,6-tris(N,N-dimethylaminomethyl)phenol as Mannich base of the formula (III).

9. A hardener for epoxy resins comprising at least one amine as claimed in claim 1.

10. A hardener for epoxy resins, comprising at least one amine as claimed in claim 1 and at least one further amine and/or at least one additive.

11. The hardener as claimed in claim 10, wherein the further amine is selected from the group consisting of 2-butyl-2-ethyl-1,5-pentanediamine, 2,2(4),4-trimethylhexamethylenediamine, 1,12-dodecandiamine, bis(4-aminocyclohexyl)methane, 1-amino-3-aminomethyl-3,5,5-trimethylcyclohexane, 1,3-bis(aminomethyl)cyclohexane, 1,4-bis(aminomethyl)cyclohexane, 2,5(2,6)-bis(aminomethyl)bicyclo[2.2.1]heptane, 3(4),8(9)-bis(aminomethyl)tricyclo[5.2.1.0$^{2,6}$]decane, 1,4-diamino-2,2,6-trimethylcyclohexane, 1,8-menthanediamine, 3,9-bis(3-aminopropyl)-2,4,8,10-tetraoxaspiro[5.5]undecane, 1,3-bis(aminomethyl)benzene, aliphatic primary di- and triamines containing ether groups, N$^1$-benzyl-1,2-propanediamine, N$^1$-(4-methoxybenzyl)-1,2-propanediamine, N-benzyl-1,3-bis(aminomethyl)benzene, N,N'-dibenzyl-1,3-bis(aminomethyl)benzene, N-2-ethylhexyl-1,3-bis(aminomethyl)benzene, N,N'-bis(2-ethylhexyl)-1,3-bis(aminomethyl)benzene, partially styrenized 1,3-bis(aminomethyl)benzene, and adducts of (i) at least one polyamine having at least three amine hydrogens that are reactive toward epoxide groups with (ii) at least one epoxide.

12. The hardener as claimed in claim 11, wherein the further amine is N$^1$-benzyl-1,2-propanediamine.

13. An epoxy resin composition comprising
a resin component comprising at least one epoxy resin, and
a hardener component comprising at least one amine as claimed in claim 1.

14. A coating obtained from an epoxy resin composition as claimed in claim 13.

15. A method for accelerating the curing of an epoxy resin composition, wherein an amine as claimed in claim 1 is added.

* * * * *